(12) United States Patent
Chen et al.

(10) Patent No.: US 8,408,797 B2
(45) Date of Patent: Apr. 2, 2013

(54) METHOD OF MANUFACTURING BEARING DEVICE COMPONENT COATED WITH PHOTOLUMINESCENCE MATERIAL, BEARING DEVICE COMPONENT AND PROCESSING DEVICE WITH AN INDICATOR DISPLAYING INFORMATION FOR A SIGNAL INCLUDING INFORMATION IN ACCORDANCE WITH LIGHT EMISSION OF A PHOTOLUMINESCENCE MATERIAL APPLIED ON BEARING DEVICE

(75) Inventors: Chenglin Chen, Suzhou (CN); Kazuhiro Matsuo, Fujieda (JP)

(73) Assignee: Alphana Technology Co., Ltd., Shizuoka Prefecture (JP)

( * ) Notice: Subject to any disclaimer, the term of this patent is extended or adjusted under 35 U.S.C. 154(b) by 0 days.

(21) Appl. No.: 13/226,676

(22) Filed: Sep. 7, 2011

(65) Prior Publication Data

US 2013/0058604 A1    Mar. 7, 2013

(51) Int. Cl.
*F16C 32/06* (2006.01)
*G08B 21/00* (2006.01)
*H01L 21/00* (2006.01)
*H01L 21/26* (2006.01)

(52) U.S. Cl. ............. 384/100; 340/682; 438/3; 438/513

(58) Field of Classification Search .................. None
See application file for complete search history.

(56) References Cited

U.S. PATENT DOCUMENTS

| 4,332,428 | A | * | 6/1982 | Maruyama | 310/90.5 |
|---|---|---|---|---|---|
| 5,013,947 | A | * | 5/1991 | Ide | 310/67 R |
| 5,215,385 | A | * | 6/1993 | Ide | 384/100 |
| 7,056,024 | B2 | * | 6/2006 | Weingord et al. | 384/100 |
| 2004/0132881 | A1 | | 7/2004 | Okamiya et al. | |
| 2005/0025403 | A1 | * | 2/2005 | Ueda et al. | 384/100 |
| 2006/0132968 | A1 | | 6/2006 | Kobayashi et al. | |
| 2008/0011551 | A1 | * | 1/2008 | Inazuka et al. | 184/54 |

FOREIGN PATENT DOCUMENTS

| JP | 2000-266052 A | 9/2000 |
|---|---|---|
| JP | 2001-027242 A | 1/2001 |

* cited by examiner

*Primary Examiner* — George Bugg
*Assistant Examiner* — Renee Dorsey
(74) *Attorney, Agent, or Firm* — Holtz, Holtz, Goodman & Chick, P.C.

(57) ABSTRACT

A method of manufacturing a bearing device component is provided. The bearing device includes a shaft and a sleeve that surrounds the shaft, and at least either one of the shaft and the sleeve is referred to as a work. The method includes: a process of forming a coating of an anti-sticking-lube polymer on the work; a process of applying a photoluminescence material to a range overlapping a range where the coating of the anti-sticking-lube polymer is formed; and a condition detecting process of causing the photoluminescence material to emit light by causing the work to be irradiated with excitation light that excites the photoluminescence material, and detecting an applied condition of the photoluminescence material based on the light emission of the photoluminescence material, thereby detecting a condition of the coating of the anti-sticking-lube polymer.

16 Claims, 6 Drawing Sheets

METHOD OF MANUFACTURING BEARING DEVICE COMPONENT COATED WITH PHOTOLUMINESCENCE MATERIAL, BEARING DEVICE COMPONENT AND PROCESSING DEVICE WITH AN INDICATOR DISPLAYING INFORMATION FOR A SIGNAL INCLUDING INFORMATION IN ACCORDANCE WITH LIGHT EMISSION OF A PHOTOLUMINESCENCE MATERIAL APPLIED ON BEARING DEVICE

BACKGROUND OF THE INVENTION

1. Field of the Invention

The present invention relates to a method of manufacturing a bearing device component coated with a photoluminescence material and a bearing device component.

2. Description of the Related Art

Fluid bearing devices are known which are built in a hard disk drive, etc. Such a fluid bearing device includes a shaft, a sleeve which surrounds and supports the shaft in a freely rotatable manner relative to each other, and a lubricant present between the shaft and the sleeve. Such a fluid bearing device may have the lubricant which is spilled from the air-liquid interface thereof and which sticks to the shaft and the sleeve, resulting in a splash.

Such a splash of the sticking lubricant is further spilled to the exterior of the bearing, and thus the exterior is contaminated. When, for example, the fluid bearing device is built in a hard disk drive, if such a splash is spilled to the exterior of the bearing and the disk or the head is contaminated, the possibility of read/write error increases.

Hence, the shaft and the sleeve have an anti-sticking-lube polymer applied at a predetermined location in order to reduce the splash of the lubricant. However, application of such an anti-sticking-lube polymer to the shaft and the sleeve may be forgotten during the manufacturing process. Hence, a scheme of forming a marking of a colorant in order to indicate that the anti-sticking-lube polymer is applied, and of causing a person to visually check the presence/absence of such a colorant is possible.

This scheme, however, depends on a visual checking of a human, so that a false inspection due to an oversight often occurs, and it takes large labor hours, and thus the work efficiency is poor. Moreover, it is difficult to visually check whether or not the coating range of the anti-sticking-lube polymer covers the minimum range or whether or not the anti-sticking-lube polymer is applied over the allowable maximum range.

SUMMARY OF THE INVENTION

The present invention has been made in view of the above-explained circumstances, and it is an object of the present invention to reduce the possibility of false inspection of the application of an anti-sticking-lube polymer and to facilitate checking of the coating range of the anti-sticking-lube polymer.

In order to achieve the above-explained object, a first aspect of the present invention provides a method of manufacturing a bearing device component, the bearing device including a shaft and a sleeve that surrounds the shaft, at least either one of the shaft and the sleeve being referred to as a work, and the method including: a process of forming a coating of an anti-sticking-lube polymer on the work; a process of applying a photoluminescence material to a range overlapping a range where the coating of the anti-sticking-lube polymer is formed; and a condition detecting process, the condition detecting process including: causing the photoluminescence material to emit light by causing the work to be irradiated with excitation light that excites the photoluminescence material; generating a signal in accordance with light emission of the photoluminescence material; inputting the signal into a processing device that determines information included in the signal; and detecting an applied condition of the photoluminescence material based on a determination result by the processing signal.

In order to achieve the above-explained object, a second aspect of the present invention provides a component for a bearing device, the component being at least either one of following: a shaft for the bearing device; and a sleeve for the bearing device, the component including: a coating of an anti-sticking-lube polymer formed on a surface of the component; and a photoluminescence material applied to a range where the anti-sticking-lube polymer coating is formed.

In order to achieve the above-explained object, a third aspect of the present invention provides a processing device used for a method of manufacturing a bearing device component, the processing device including: signal generating means; and an indicator, the signal generating means generating a signal including information in accordance with light emission of a photoluminescence material applied on the bearing device component, and the indicator displaying information included in the signal.

An arbitrary combination of the above-explained structural elements and replacement of the structural element or the expression of the present invention among a method, an apparatus, and a system are also effective as the present invention.

DETAILED DESCRIPTION OF THE PREFERRED EMBODIMENTS

Figure 1:
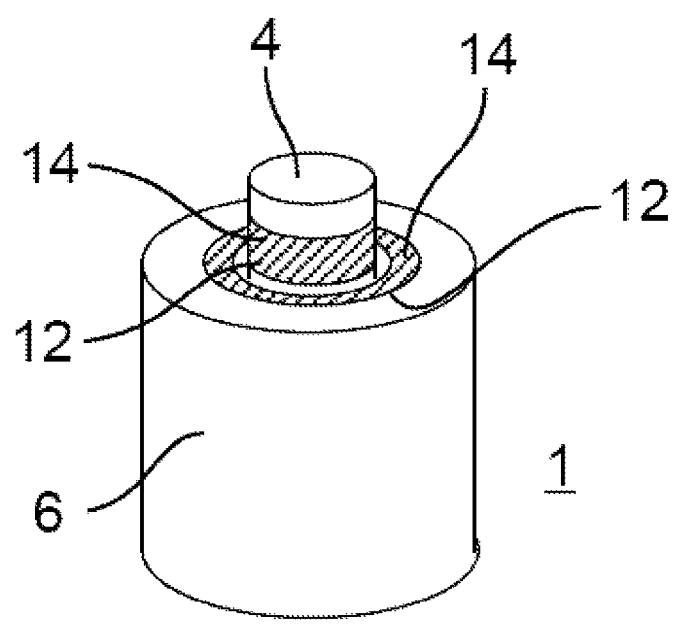
FIG. 1 is a perspective view showing a general structure of a bearing device including a shaft and a sleeve both for a bearing device according to an embodiment.

Preferred embodiments of the present invention will be explained below with reference to the accompanying drawings. The same and equivalent structural element and component in respective drawings will be denoted by the same reference numeral, and the duplicated explanation thereof will be omitted. Moreover, the dimension of each component in each drawing is enlarged or reduced in size as needed in order to facilitate understanding. Furthermore, some of the components not fundamental for explaining the embodiments of the present invention will be drawn in a simplified manner in each drawing.

Figure 2:
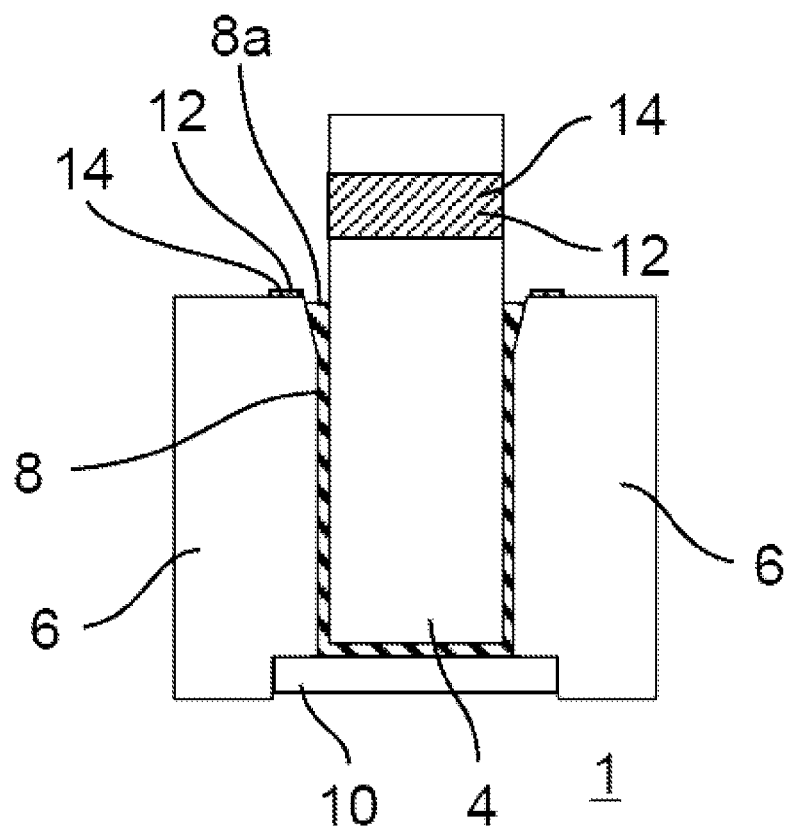
FIG. 2 is a cross-sectional view showing a general structure of the bearing device shown in FIG. 1.

FIG. 1 is a perspective view showing a general structure of a bearing device including a shaft and a sleeve both for a bearing device according to an embodiment. FIG. 2 is a cross-sectional view showing a general structure of the bearing device shown in FIG. 1. As shown in the drawings, a bearing device 1 includes a shaft 4, a sleeve 6, a lid member 10 that plugs off the bottom end of the sleeve 6, and a lubricant 8. The shaft 4 is surrounded by the sleeve 6 and is supported in a manner mutually rotatable. An unillustrated radial dynamic pressure groove is formed in either one of the outer circumference surface of the shaft 4 or the inner circumference surface of the sleeve 6. The lid member 10 is bonded and fixed to a recess formed at the bottom end of the sleeve 6. The lubricant 8 is present between the shaft 4 and the sleeve 6. Upon mutual rotation of the shaft 4 and the sleeve 6, the lubricant 8 produces a dynamic pressure because of an action of the radial dynamic pressure groove. This dynamic pressure supports the shaft 4 in the sleeve 6 in the radial direction. The lubricant 8 forms an air-liquid interface 8a that is a boundary with air between the shaft 4 and the sleeve 6.

The following explanation will be given based on a definition that defines the side where the lid member 10 is coupled to the sleeve 6 is a bottom side. Moreover, the shaft 4 and the sleeve 6 may be referred to as a work 100 in some cases in the following explanation.

Figure 3:
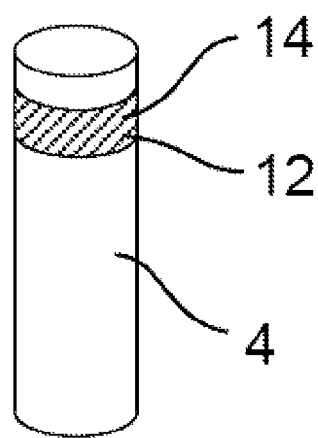
FIG. 3 is a perspective view showing the general structure of the shaft of the bearing device shown in FIG. 1.

FIG. 3 is a perspective view showing a general structure of the shaft 4 of the bearing device 1 of FIG. 1. The shaft 4 can be formed of various materials in a substantially cylindrical shape. For example, a stainless steel like SUS420J2 in the JIS is used as a base material, and is processed by, for example, a so-called center-less polishing and formed in a predetermined shape. In order to obtain a desired toughness, a thermal treatment like annealing may be performed on such a material.

The shaft 4 is coated with a stripe-shaped anti-sticking-lube polymer 12 at a portion above the position of the air-liquid interface 8a. Various kinds of anti-sticking-lube polymers can be used as the anti-sticking-lube polymer 12 of the embodiment. For example, a polyester-based anti-sticking-lube polymer and a fluorine-based anti-sticking-lube polymer are preferable from the standpoint of the easiness of coating. The anti-sticking-lube polymer is dispersed in a solvent, applied to a predetermined area of the shaft 4, and heated, thereby forming the coating of the anti-sticking-lube polymer 12. The solvent is not limited to any particular one. For example, ether or alcohol can be used. In the present embodiment, hydrofluoroether, such as a methyl-nonafluoro-isobutyl-ether or a methyl-nonafluoro-butyl-ether, is used. Such ether is preferable since it is not ignitable. The thermal treatment condition can be set on the basis of a test with the solvent, the temperature of thermal treatment, the time thereof, and the dispersed concentration of the anti-sticking-lube polymer being as parameters.

Figure 4:
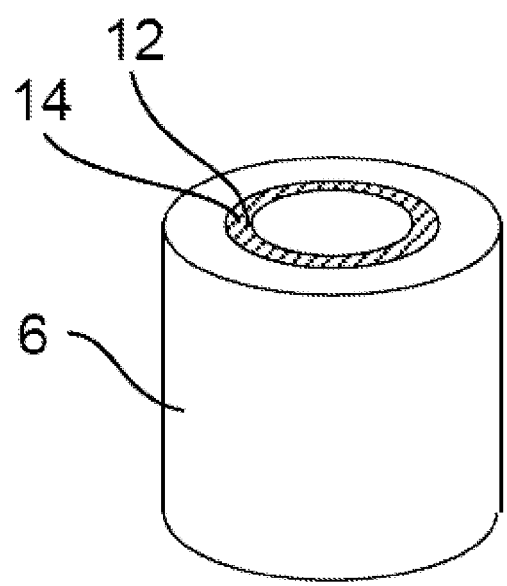
FIG. 4 is a perspective view showing the general structure of the sleeve of the bearing device shown in FIG. 1.

FIG. 4 is a perspective view showing a general structure of the sleeve 6 of the bearing device 1 of FIG. 1. The sleeve 6 can be formed of a metal, such as brass or stainless steel, or a resin material. The sleeve 6 can be formed of brass, etc., cut and formed in a hollowed and substantially cylindrical shape. In order to obtain a desired toughness, a surface treatment like electroless plating may be performed. The sleeve 6 has a pair of unillustrated radial dynamic pressure grooves which are in a herringbone shape and which are formed up and down in the inner circumference surface of the sleeve 6. The radial dynamic pressure grooves can be formed by, for example, rolling.

The sleeve 6 is coated with the anti-sticking-lube polymer 12 applied 360 degrees at an upper end surface of the sleeve 6. The same material and technique as those applied to the shaft 4 can be used for the anti-sticking-lube polymer 12 of the sleeve 6.

During a process of applying the anti-sticking-lube polymer 12, such a coating may become unsuccessful due to a trouble of the process. For example, when such a coating is hardly fixed, the range of such a coating becomes narrower than a predetermined minimum range or larger than a maximum range. When the anti-sticking-lube polymer 12 is colorless, it is difficult to detect a work 100 with a defective coating. In order to overcome such a problem, the work 100 has a photoluminescence material applied at a range overlapping the range where the coating of the anti-sticking-lube polymer 12 is formed. By inspecting whether or not the photoluminescence material is applied, it becomes possible to detect the work 100 with the defective coating of the anti-sticking-lube polymer 12. The work 100 with the defective coating is eliminated or repaired, so that the possibility that a product built with such a work 100 is delivered to the market can be reduced.

When the photoluminescence material is irradiated with excitation light like ultraviolet, electrons are excited to a high-energy orbit. When the excited electrons return to the original orbit, the photoluminescence material causes a luminescence phenomenon of emitting light with unique spectrum to that photoluminescence material. The photoluminescence material is not limited to any particular one. In the present embodiment, a phosphor, such as zinc sulfide or an aluminate compound, is used. It is preferable since the lifetime of emitted light is long and application of such phosphor is easy.

In the example case shown in FIG. 3, the shaft 4 has a phosphor 14 applied at a range overlapping the coating range of the anti-sticking-lube polymer 12. The sleeve 6 shown in FIG. 4 has the phosphor 14 applied at a range overlapping the coating range of the anti-sticking-lube polymer 12. The phosphor 14 dispersed in a solvent can be applied. The solvent is not limited to any particular one. For example, ether or alcohol can be used. In the present embodiment, hydrofluoroether, such as methyl-nonafluoro-isobutyl-ether or methyl-nonafluoro-butyl-ether, is used. Such ether is preferable since it is not ignitable. The solvent can be heated and volatilized.

Figure 5:
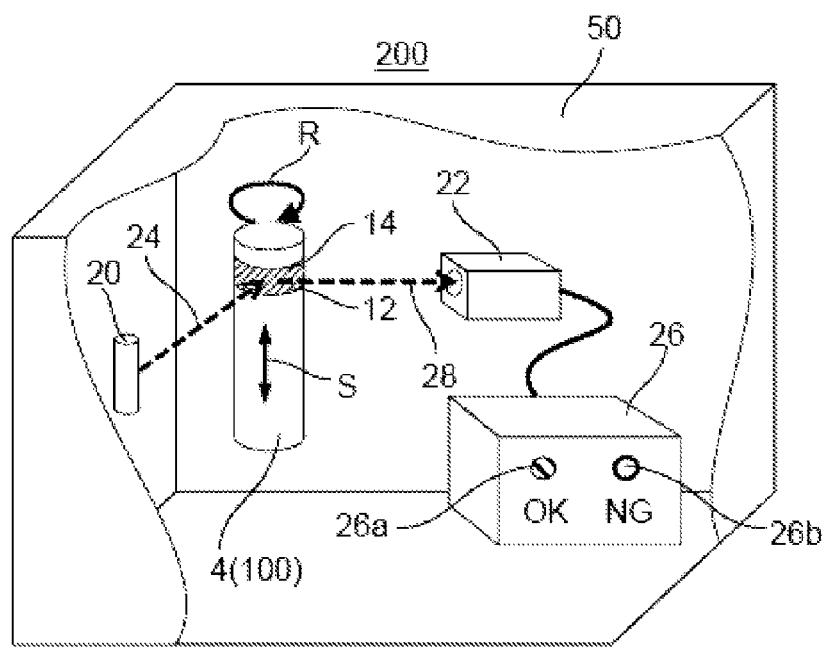
FIG. 5 is a perspective view showing the outline of a signal detecting process in a manufacturing method according to the embodiment.

Next, an explanation will be given of a process of detecting the work 100 with a defective coating. FIG. 5 is a perspective view showing an outline of a signal detecting process 200 of detecting the shaft 4 that is an example of the work 100 with a defective coating in a manufacturing method of a bearing device component according to the present embodiment.

First, the shaft 4 coated with the phosphor 14 is placed at a dark space. For example, a dark room 50 is available. In FIG. 5, an external wall is partially omitted in order to facilitate understanding for the interior of the dark room 50. A light emitting device 20 emits excitation light 24 to a region where the phosphor 14 is applied and the periphery therearound while the shaft 4 is being rotated in a direction indicated by an arrow R. In the present embodiment, the excitation light 24 used is ultraviolet. When irradiated with the excitation light 24, the phosphor 14 emits phosphorescence 28. The phosphorescence 28 at the region where the phosphor 14 is applied and the periphery therearound is detected by an optical sensor 22 while the shaft 4 is being rotated in the direction indicated by the arrow R. That is, the shaft 4 is successively inspected in the circumferential direction.

The phosphorescence 28 contains spectrum light unique to the phosphor 14. The optical sensor 22 (signal generating means) detects the spectrum light (wavelength: from 525 to 590 nm, but it is practical within a range from 430 to 620 nm) unique to the phosphor 14, and outputs an output signal with a signal intensity in accordance with the intensity of the spectrum light. In the present embodiment, a signal processing device 26 includes a processor, and a memory storing a program. By running such a program, when the output signal has a signal intensity (i.e., information included in the output signal) equal to or greater than a predetermined value, the signal processing device 26 displays an OK indication 26a, and when the output signal 30 is not in the predetermined state, the signal processing device 26 displays an NG (No Good) indication 26b. When the NG indication 26b is displayed, the shaft 4 is eliminated from the manufacturing process or repaired. As a result, the possibility that a product built with such a shaft 4 is delivered to the market can be reduced. The same signal detecting process 200 can be applied when the work 100 is the sleeve 6.

Since the signal detecting process 200 is carried out while the work 100 is being rotated, the coating 12 partially defective in the circumferential direction can be detected.

The signal detecting process 200 may be carried out while the measuring point of the optical sensor 22 is being moved in the axial direction as is indicated by an arrow S of the work 100. It is advantageous that when the coating 12 is partially defective in the axial direction, such a defect can be detected.

The signal detecting process 200 may detect the phosphorescence 28 point by point intermittently in the circumferential direction of the work 100. In the present embodiment, the phosphorescence 28 is successively detected in the circumferential direction of the work 100. It is advantageous that when the coating 12 has a slight defect in the circumferential direction, such a defect can be detected.

The signal detecting process 200 can be carried out in a space where external light enters, but in this case, external light other than the phosphorescence 28 inputs in the optical sensor 22 and noises may be superimposed on the output signal 30. Such noises may possibly cause the signal processing device 26 to display a false indication. Hence, according to the present embodiment, the signal detecting process 200 is carried out in the dark room 50. This reduces the possibility of false indication when the phosphorescence 28 is weak. Moreover, the signal detecting process 200 may be carried out in a clean air space where particles suspended in the atmosphere are reduced. In the present embodiment, the dark room 50 is filled with clean air. This reduces the possibility that particles stick to the work 100 and the work 100 is contaminated.

Figure 6:
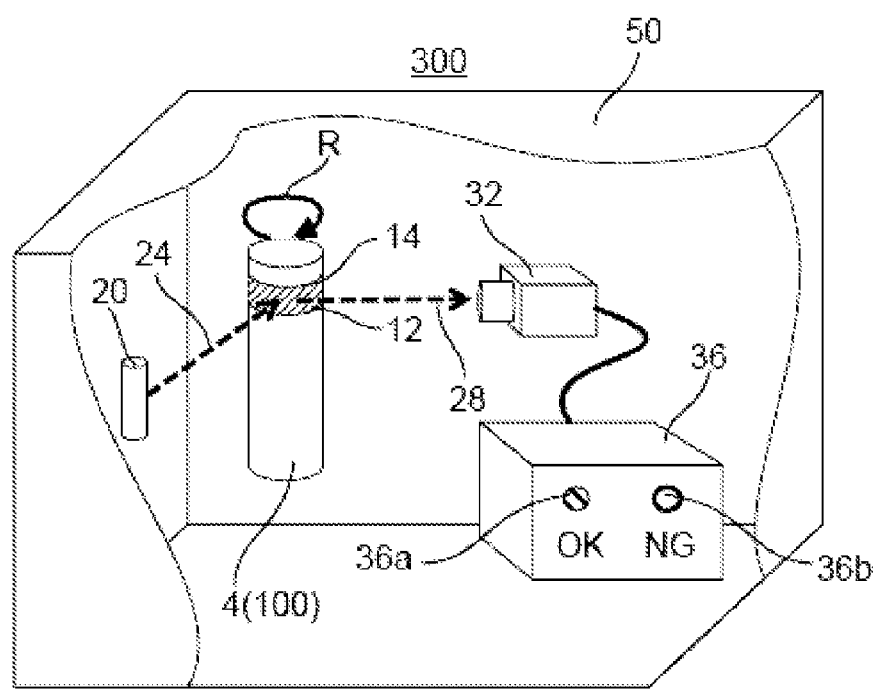
FIG. 6 is a perspective view showing the outline of an image detecting process in a manufacturing method according to another embodiment.

Next, an explanation will be given of an image detecting process 300 of detecting the work 100 with a defective coating according to another embodiment. FIG. 6 is a perspective view showing an outline of the image detecting process 300 of detecting the shaft 4 which is an example work 100 and which has a defective coating in a manufacturing method of a bearing device component according to another embodiment. The image detecting process 300 has the same procedures as those of the signal detecting process 200 up to emission of the excitation light 24 to the phosphor 14 in order to cause the phosphor 14 to emit the phosphorescence 28, and the duplicated explanation will be omitted.

The image detecting process 300 causes a camera 32 (signal generating means) to pick up images of the region where the phosphor 14 is applied and the periphery therearound while the shaft 4 is being rotated, and to convert the images into image signals, and causes an image processing device 36 to capture the image signals. That is, successive images of the shaft 4 around the circumferential direction are captured. The camera 32 converts the captured images into image signals, and inputs the image signals into the image processing device 36. The image processing device 36 detects information on an applied range of the phosphor 14 in accordance with the image signals. In the present embodiment, the image processing device 36 includes a processor, and a memory storing a program. By running such a program, the following function is realized. That is, applied range information of the phosphor 14 is detected based on a region of the image (image signal) containing spectrum light unique to the phosphor 14. Moreover, when the applied range information covers the minimum applied range, an OK indication 36a is displayed, and when the applied range information does not cover the minimum applied range, an NG indication 36b is displayed.

The anti-sticking-lube polymer 12 may be applied on a region contacting the air-liquid interface 8a of the lubricant 8 beyond the predetermined maximum allowable range of the work 100. When the coating is formed beyond such a region, the capillary force of the work 100 decreases and the lubricant 8 is likely to be spilled. Hence, according to the present embodiment, the image detecting process 300 causes the image processing device 36 to display whether or not the applied range information exceeds the predetermined maximum allowable range. Accordingly, it becomes possible to detect the work 100 having the coating exceeding the predetermined maximum allowable range. More specifically, when the applied range information exceeds the predetermined maximum allowable range, the NG indication 36b is displayed regardless of the fact whether or not the applied range information covers the predetermined minimum applied range.

When the NG indication 36b is displayed, the shaft 4 is eliminated from the manufacturing process or repaired. Accordingly, the possibility that a product built with such a shaft 4 is delivered to the market can be reduced. The same image detecting process 300 can be applied when the work 100 is the sleeve 6.

The image detecting process 300 is carried out while the work 100 is being rotated in a direction indicated by an arrow R, so that when the coating 12 is partially defective in the circumferential direction, such a defect can be detected.

In the image detecting process 300, successive images are captured in the circumferential direction of the work 100. Accordingly, it is advantageous that when the coating 12 is slightly defective in the circumferential direction, such a defect can be detected.

The image detecting process 300 can be carried out in a bright space where external light enters, but when external light other than the phosphorescence 28 enters the camera 32, noises may be superimposed on the captured images. Such noises may possibly cause the image processing device 36 to display a false indication. Hence, according to the present embodiment, the image detecting process 300 is carried out in the dark room 50. This reduces the possibility of false indication when the phosphorescence 28 is weak. Moreover, the image detecting process 300 may be carried out in a space filled with clean air like a clean room where particles suspended in the atmosphere are reduced. In the present embodiment, the dark room 50 is provided in a clean room filled with clean air. This reduces the possibility that particles stick to the work 100 and the work 100 is contaminated.

The present invention employing the above-explained structure has following advantages.

According to the present invention, a process of detecting the work 100 with a defective coating 12 is mechanized. The defect in coating 12, i.e., the percent defective of the work 100 is normally extremely low. When such an inspection with extremely low percent defective is carried out by a human through a visual checking, the possibility of overlooking that the defective work 100 is let gone through the inspection becomes high, and thus the certainty becomes an issue. However, mechanization of such a process reduces the possibility of overlooking, thereby improving the certainty.

It is desirable to carry out the process of detecting the phosphorescence 28 in a dark space. However, when a human keeps watching phosphorescence 28 in a dark space, the eyes must be fatigued. However, when the phosphorescence 28 is detected by a machine, such an issue does not occur.

In practice, the work 100 is produced within a short time such as five seconds per work. In order to detect the phosphorescence 28, an inspection within a time shorter than such a time becomes necessary. When this process is carried out by a human through a visual checking, the possibility of inspection oversight may increase due to a fatigue. Conversely, when the inspection time is set to be long, it is necessary to additionally employ a person for the inspection, so that the production cost increases and an additional space for the inspector becomes necessary. According to the present invention, however, such a process is mechanized, the above-explained issue does not occur, resulting in the improvement of the production efficiency.

Since the work 100 is a small component, when inspection is carried out by a human through a visual checking, what the human can do at all is to inspect whether or not the anti-sticking-lube polymer 12 is applied, and it is difficult for a human to inspect whether or not the coating range is actually covered or whether or not the anti-sticking-lube polymer 12 is applied at a range where the anti-sticking-lube polymer 12 must not be applied. Hence, the use of a microscope can be thought in the case of the visual checking by a human, but it takes a long time for the inspection. In this point, the mechanized process does not bring about such an issue.

In general, when ultraviolet with high energy is used as the excitation light, the phosphor 14 brightly emits light. However, it is not realistic in practice that a human keeps watching a reflected light of ultraviolet for a long time. However, mechanized process does not bring about such an issue.

The present invention was explained based on the embodiments, but it should be understood that the embodiments of the present invention teach the principle and application of the present invention. It should be also understood that the embodiments of the present invention include various changes and modifications without departing from the scope and spirit of the present invention.

For example, in the above-explained embodiments, the explanation was given of the case in which the photoluminescence material that is the phosphor 14 is applied separately from the anti-sticking-lube polymer 12, but the present invention is not limited to this configuration. For example, the phosphor 14 as the photoluminescence material may be applied together with the anti-sticking-lube polymer 12.

What is claimed is:

1. A method of manufacturing a bearing device component, the bearing device including a shaft and a sleeve that surrounds the shaft, at least either one of the shaft and the sleeve being referred to as a work, and the method comprising:
   a process of forming a coating of an anti-sticking-lube polymer on the work;
   a process of applying a photoluminescence material to a range overlapping a range where the coating of the anti-sticking-lube polymer is formed; and
   a condition detecting process, the condition detecting process including:
      causing the photoluminescence material to emit light by causing the work to be irradiated with excitation light that excites the photoluminescence material;
      generating a signal in accordance with light emission of the photoluminescence material;
      inputting the signal into a processing device that determines information included in the signal; and
      detecting an applied condition of the photoluminescence material based on a determination result by the processing signal.

2. The method according to claim 1, wherein the condition detecting process includes a signal detecting process of:
   emitting the excitation light that excites the photoluminescence material to the work;
   detecting light emitted from the photoluminescence material and including a spectrum unique to the photoluminescence material through an optical sensor; and
   displaying an indication whether or not the photoluminescence material is applied in accordance with an output signal by the optical sensor.

3. The method according to claim 2, wherein the signal detecting process is carried out while the work is being rotated.

4. The method according to claim 2, wherein the signal detecting process is carried out while a measuring point of the optical sensor is being moved in a direction of a rotational axis of the work.

5. The method according to claim 2, wherein the signal detecting process detects emitted light successively in a circumferential direction of the work.

6. The method according to claim 2, wherein the signal detecting process is carried out in a dark room.

7. The method according to claim 2, wherein the signal detecting process is carried out in a space filled with clean air.

8. The method according to claim 2, wherein the photoluminescence material is a phosphor.

9. The method according to claim 1, wherein the condition detecting process includes an image detecting process of:
   emitting the excitation light that excites the photoluminescence material to the work;
   causing a camera to convert an image of a region of the work where the photoluminescence material is applied into an image signal and to input the image signal into an image processing device;
   causing the image processing device to detect applied range information on the photoluminescence material in accordance with the image signal; and
   displaying an indication whether or not the applied range information covers a predetermined minimum applied range.

10. The method according to claim 9, wherein the image detecting process is carried out while the work is being rotated.

11. The method according to claim 9, wherein the image detecting process captures images successively in a circumferential direction of the work.

12. The method according to claim 9, wherein the image detecting process is carried out in a dark room.

13. The method according to claim 9, wherein the image detecting process is carried out in a space filled with clean air.

14. The method according to claim 9, wherein the image detecting process displays an indication whether or not the applied range information exceeds a predetermined maximum application allowable range.

15. The method according to claim 9, wherein the photoluminescence material is a phosphor.

16. A processing device used for a method of manufacturing a bearing device component, the processing device comprising:
   signal generating means; and
   an indicator, the signal generating means generating a signal including information in accordance with light emission of a photoluminescence material applied on the bearing device component, and the indicator displaying information included in the signal.

* * * * *